US008368896B1

(12) United States Patent  (10) Patent No.: US 8,368,896 B1
Li et al.  (45) Date of Patent: Feb. 5, 2013

(54) MEASUREMENT OF SULFUR TRIOXIDE VIA SPECTROSCOPY

(75) Inventors: Yongquan Li, Schenectady, NY (US); Jeffrey S. Socha, Boylston, MA (US); Dieter Kita, Blackstone, MA (US)

(73) Assignee: Thermo Fisher Scientific Inc., Waltham, MA (US)

( * ) Notice: Subject to any disclaimer, the term of this patent is extended or adjusted under 35 U.S.C. 154(b) by 367 days.

(21) Appl. No.: 12/693,293

(22) Filed: Jan. 25, 2010

(51) Int. Cl.
*G01B 11/00* (2006.01)
*F23N 5/08* (2006.01)

(52) U.S. Cl. ............... 356/437; 250/573; 250/339.08; 250/343; 356/439; 356/388; 431/79

(58) Field of Classification Search .......... 356/437–439; 250/339.01, 339.06–339.08, 343
See application file for complete search history.

(56) References Cited

PUBLICATIONS

Chrysostom, Engelene, Nicolaie Vulpanovici, Tony Masiello, Jeffrey Barber, Joseph Nibler, Alfons Weber, Arthur Maki, Thomas Blake "Coherent Raman and INfrared Studies of Sulfur Trioxide", Journal of Molecular Spectroscopy 210, 233-239 (2001).*

Sharpe, Steven W., et al., "The v3 and 2v3 bands of 32S16O3, 32S18O3, 34S16O3, and 34S18O3", Journal of Molecular Spectroscopy 222 (2003), Received Mar. 7, 2003, revised Jul. 30, 2003, pp. 1-11.

Rawlins, W.T., et al., "A Quantum Cascade Laser Sensor for SO2 and SO3 for Application to Combustor Exhaust Streams", Laser Diagnostics for Gasdynamic, Applied Optics 44(31), Nov. 2005, pp. 1-33.

Maki, Arthur, et al., "High Resolution Infrared Spectra of the v2, v3, v4, and 2v3 Bands of 32S16O3", Journal of Molecular Spectroscopy 210, 240-249 (2001), Received Jul. 10, 2001, revised Sep. 14, 2001, published online Nov. 16, 2001, pp. 1-10.

* cited by examiner

*Primary Examiner* — Gregory J Toatley
*Assistant Examiner* — Rebecca C Bryant
(74) *Attorney, Agent, or Firm* — Chapin IP Law, LLC (57) ABSTRACT

Configurations herein include a novel process, system, etc., to measure a concentration of sulfur trioxide in a gas sample including sulfur trioxide, sulfur dioxide, and water. An example system can include an optical radiation source that generates an optical signal at a plurality of vibration-rotation transitions around at least one frequency selected from the group consisting of 1396.889 $cm^{-1}$, 1396.908 $cm^{-1}$, 1396.962 $cm^{-1}$, 1397.003 $cm^{-1}$, 1397.037 $cm^{-1}$, 1397.047 $cm^{-1}$, and 1397.052 $cm^{-1}$. The optical signal is transmitted along an optical path through the gas sample. Based on adjusting a pressure of the gas sample, each of the plurality of vibration-rotation absorption transitions associated with the sulfur trioxide can be substantially isolated from interfering absorption by the sulfur dioxide and the water vapor in the gas sample. Based on a spectral analysis, the system generates a value indicative of a concentration of sulfur trioxide in the gas sample.

20 Claims, 9 Drawing Sheets

MEASUREMENT OF SULFUR TRIOXIDE VIA SPECTROSCOPY

BACKGROUND

Emissions such as flue gases from fossil fuel from combustion facilities of coal-fired utilities and municipal solid waste incinerators typically include sulfur trioxide (i.e., $SO_3$). Coal and petroleum fuels usually contain sulfur compounds. Combusting coal and petroleum typically results in generation of sulfur dioxide (i.e., $SO_2$).

Combustion facilities typically operate pollution control devices to remove nitrogen monoxide and nitrogen dioxide (NOx). A side effect of operating NOx control devices (Selective Catalytic Reduction SCR) is the generation of sulfur trioxide. In the SCR, a portion of the sulfur dioxide emission is typically oxidized, resulting in sulfur trioxide. Sulfur trioxide has a strong affinity for water, and, in the presence of moisture and low temperatures, easily converts into sulfuric acid ($H_2SO_4$). In ambient conditions, typically all $SO_3$ is converted into $H_2SO_4$, such that there is almost no presence of $SO_3$ in air.

Sulfur trioxide emissions are undesirable for several reasons. As briefly mentioned, sulfur trioxide and/or sulfuric acid exiting a stack or chimney can result in pollution such as acid rain. Sulfur trioxide can be very corrosive to equipment used in combustion facilities.

Selective catalytic reduction processes used to reduce pollutants in a flue gas can have the effect of creating higher levels of sulfur trioxide in a flue gas. Such higher levels of sulfur trioxide have been known to adversely affect removal of certain pollutants. For example, mercury is commonly removed from flue gases using activated carbon as part of an adsorption process. With higher levels of sulfur trioxide present during the adsorption process, the percent of mercury removed from a flue gas typically decreases.

There are several types of conventional detection systems that can be used to detect a presence of sulfur trioxide. Such systems include Fourier transform infrared (FTIR) spectroscopy, tunable diode laser spectroscopy (TDL), acid dew-point, conversion-fluorescence, filter-correlation, and cavity ring-down spectroscopy.

There have been attempts to use FTIR and tunable diode laser spectroscopy to measure sulfur trioxide. Compared with TDL, FTIR showed less sensitivity and might not be feasible for monitoring sulfur trioxide in stack gas. Acid dew-point and conversion-fluorescence methods could not distinguish between sulfuric acid and sulfur trioxide and also suffer severe interferences. Like FTIR, filter-correlation may not be sensitive enough for measuring sulfur trioxide as continuous environmental monitoring system (CEMS). Cavity ring-down spectroscopy is a very sensitive and highly selective technology for gas sensing. It relies on very high minor reflectivity (larger than 99.99%) for its up to $10^4$ optical passes. The highly contaminated gas samples might quickly deteriorate the minor reflectivity and potentially limit its application to the stack gas monitoring. Accordingly, such techniques may not be useful for detecting $SO_3$.

By and large, most conventional systems measure an amount of sulfuric acid in a sample and then use such a measurement to infer an amount of sulfur trioxide in a gas sample. Measuring sulfuric acid is so common that many of today's systems claim to measure an amount of sulfur trioxide, yet in reality, such systems actually measure an amount of sulfuric acid in a sample to infer an amount of sulfur trioxide. In other words, many "$SO_3$" measurements in the prior art are inferred through surrogate measurements of $H_2SO_4$.

SUMMARY

As an acid rain precursor, sulfur trioxide is a very reactive and highly corrosive gas species. It can quickly react with water moisture to produce sulfuric acid. This tendencyposes a real challenge to accurately a concentration of sulfur trioxide in a sample. Recently, an increasing demand for the emission control and industrial processing monitoring has driven the development of sulfur trioxide detection systems.

Techniques discussed herein significantly overcome the challenges of detecting an amount of sulfur trioxide present in a sample. For example, embodiments herein include controlling one or more system parameters to prevent the sulfur trioxide from converting into sulfuric acid and then performing a specific type of spectral analysis of the gas sample to directly measure a concentration of sulfur trioxide.

More specifically, embodiments herein include a novel process, system, etc., to measure a concentration of sulfur trioxide in a gas sample including sulfur trioxide, sulfur dioxide, and water. An example system can include an optical radiation source that generates an optical signal at one or more vibration-rotation transitions around 1397 $cm^{-1}$ such as between 1396 and 1398 $cm^{-1}$.

In more specific embodiments, the optical signal is generated at least one frequency selected from the group consisting of 1396.889 $cm^{-1}$, 1396.908 $cm^{-1}$, 1396.962 $cm^{-1}$, 1396.944 $cm^{-1}$, 1396.958 $cm^{-1}$, 1396.962 $cm^{-1}$, 1397.003 $cm^{-1}$, 1397.037 $cm^{-1}$, 1397.047 $cm^{-1}$, or 1397.052 $cm^{-1}$. These frequencies correspond to frequencies at which there is substantially no absorption of the optical signal by sulfur dioxide (which may cause an interference with the $SO_3$ measurement). During operation, the optical source transmits the optical signal along an optical path through the gas sample. At reduced pressures, each of the plurality of vibration-rotation absorption transitions can be substantially isolated from interfering absorption by the sulfur dioxide and the water vapor in the gas sample. Based at least in part on an amount of the optical signal absorbed by the sulfur trioxide in the gas sample at one or more peak sulfur trioxide absorption frequencies, an analyzer according to embodiments herein generates a concentration value indicative of an amount of sulfur trioxide in the gas sample.

These and other more specific embodiments are discussed later in this specification.

It is to be understood that the system, method, apparatus, etc., as discussed herein can be embodied strictly as hardware, as a hybrid of software and hardware, or as software alone such as within a processor, or within an operating system or a within a software application.

As discussed above, techniques herein are well suited for use in chemical analyzer systems. However, it should be noted that embodiments herein are not limited to use in such applications and that the techniques discussed herein are well suited for other applications as well.

Additionally, note that although each of the different features, techniques, configurations, etc., herein may be discussed in different places of this disclosure, it is intended, where appropriate, that each of the concepts can optionally be executed independently of each other or in combination with each other. Accordingly, the one or more present inventions as described herein can be embodied and viewed in many different ways.

Also, note that this preliminary discussion of embodiments herein purposefully does not specify every embodiment and/or incrementally novel aspect of the present disclosure or claimed invention(s). Instead, this brief description only presents general embodiments and corresponding points of novelty over conventional techniques. For additional details and/or possible perspectives (permutations) of the invention(s), the reader is directed to the Detailed Description section and corresponding figures of the present disclosure as further discussed below.

BRIEF DESCRIPTION OF THE DRAWINGS

The foregoing will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION

Embodiments herein include a novel process, system, software, etc., for calculating a concentration of sulfur trioxide in a gas sample including sulfur trioxide, sulfur dioxide, and water. For example, an optical radiation source generates an optical signal at around 1397 cm$^{-1}$. The frequency of the optical signal can be one or more frequencies selected from the group consisting of 1396.889 cm$^{-1}$, 1396.908 cm$^{-1}$, 1396.944 cm$^{-1}$, 1396.958 cm$^{-1}$, 1396.962 cm$^{-1}$, 1397.003 cm$^{-1}$, 1397.037 cm$^{-1}$, 1397.047 cm$^{-1}$ or 1397.052 cm$^{-1}$.

These frequencies around 1397 cm$^{-1}$ correspond to frequencies at which there is little or substantially no absorption of the optical signal by sulfur dioxide and/or water. The optical source transmits the optical signal along an optical path through the gas sample. Based on adjusting a pressure of the gas sample being analyzed, each of the plurality of vibration-rotation absorption transitions can be substantially isolated from interfering absorption by the sulfur dioxide and the water vapor in the gas sample. Based at least in part on an amount of the optical signal absorbed by the sulfur trioxide in the gas sample at one or more peak sulfur trioxide absorption frequencies, an analyzer according to embodiments herein generates a concentration value indicative of an amount of sulfur trioxide in the gas sample.

Figure 1:
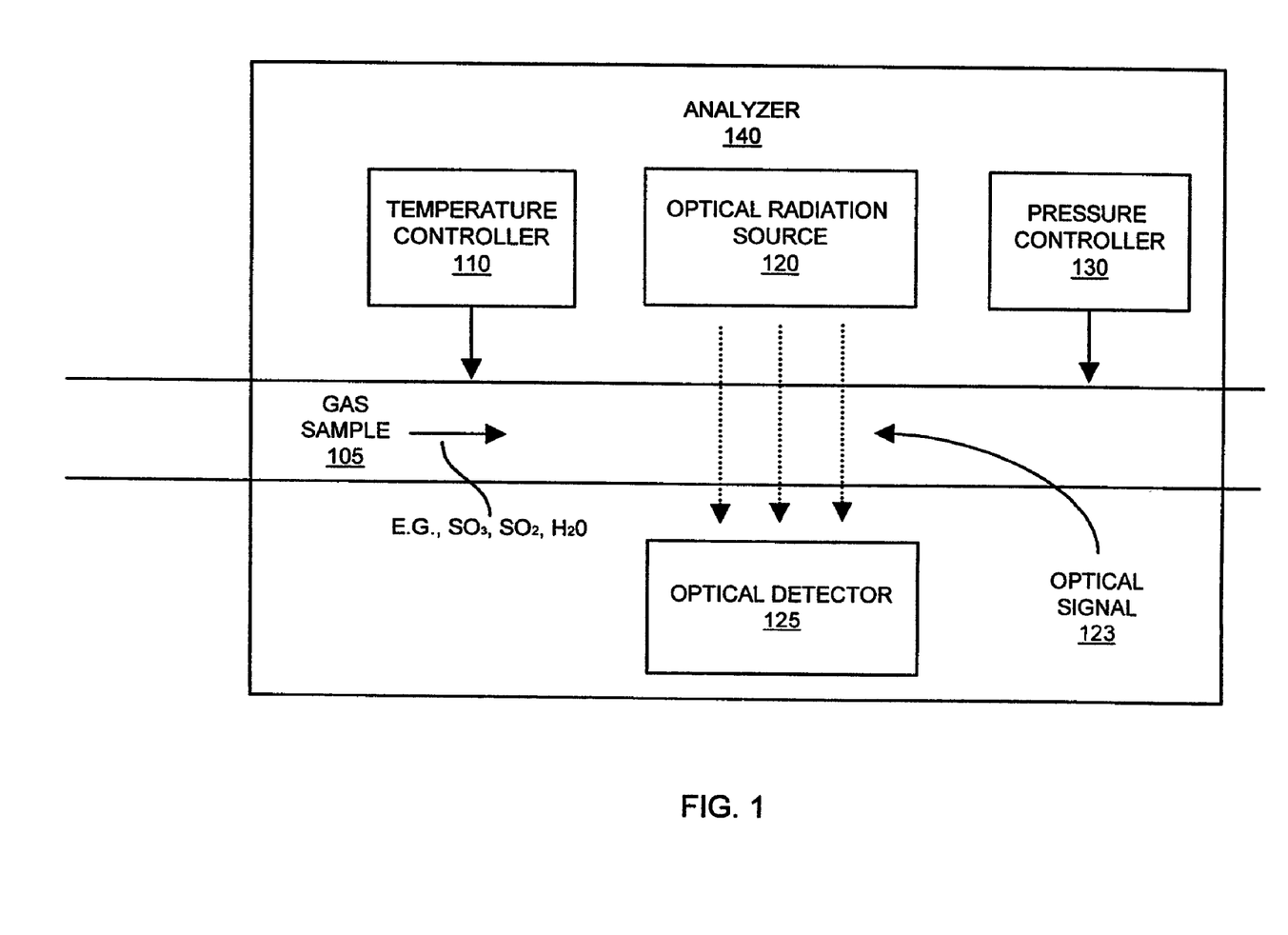
FIG. 1 is an example diagram illustrating an analyzer for calculating a concentration of sulfur trioxide according to embodiments herein.

Now, more specifically, FIG. 1 illustrates an analyzer 140 according to embodiments herein. As shown, analyzer 140 includes a temperature controller 110, optical radiation source 120, pressure controller 130, and optical detector 125. During operation, temperature controller 110 controls a temperature of the gas sample 105. Pressure controller 130 controls a pressure of the gas sample 105. Optical radiation source 120 generates optical signal 123 for transmission through gas sample 105. All or a portion of the optical signal 123 passes through the gas sample 105 and strikes optical detector 125 depending on a concentration of sulfur trioxide in the gas sample 105.

In one embodiment, the gas sample optical detector 125 can optionally include one or more optical fibers for remote detection and measurement(s) at a single location or multiple locations. Use of optical fibers makes it possible for analyzer 140 to remotely detect absorption of optical energy at one or more locations along a conduit through which the gas sample 105 travels.

By way of a non-limiting example, the gas sample 105 can be a flue gas received from a smokestack. In such an embodiment, the analyzer 140 can be used to measure the concentration of sulfur trioxide gas in the presence of large amounts of background sulfur dioxide and water vapor. For example, the gas sample 105 can include large amounts of sulfur dioxide and water. As discussed herein, analyzer 140 utilizes absorption information produced by optical detector 125 to derive a value indicative of a concentration of sulfur trioxide in the gas sample 105.

In one embodiment, the analyzer is capable of spectrally interrogating sulfur trioxide transitions in vibration-rotation absorption bands at multiple strong absorption peaks (e.g., around 1397 cm$^{-1}$ in which there are peak absorption values such as 1396.889 cm$^{-1}$, 1396.908 cm$^{-1}$, 1396.962 cm$^{-1}$, 1396.944 cm$^{-1}$, 1396.958 cm$^{-1}$, 1396.962 cm$^{-1}$, 1397.003 cm$^{-1}$, 1397.037 cm$^{-1}$, 1397.047 cm$^{-1}$, and/or 1397.052 cm$^{-1}$). During a measurement of the optical signal 123 by the optical detector 125, the sulfur trioxide transitions are substantially isolated from interfering absorption from the sulfur dioxide and the water vapor. For example, according to one embodiment, the analyzer 140 performs a spectral absorption analysis of sulfur trioxide transitions at the frequencies substantially near peak sulfur trioxide absorption frequency 1396.889 cm$^{-1}$, 1396.908 cm$^{-1}$, 1396.962 cm$^{-1}$, 1396.944 cm$^{-1}$, 1396.958 cm$^{-1}$, 1396.962 cm$^{-1}$, 1397.003 cm$^{-1}$, 1397.037 cm$^{-1}$, 1397.047 cm$^{-1}$, or 1397.052 cm$^{-1}$. Analyzing the gas sample 105 for presence of sulfur trioxide at these frequencies avoids interfering absorption from sulfur dioxide and water vapor. In other words, sulfur dioxide and water maybe present in the gas sample 105 as discussed above. However, these constituents (i.e., sulfur dioxide and water) absorb little or no radiation at or around these peaks.

In one embodiment, the optical radiation source 120 is a laser configured to generate optical signal 123 at one or more infrared frequencies. The optical radiation source 120 can generate the optical signal 123 at a power level such as 10 milliwatts although any suitable power level can be used in accordance with embodiments herein.

To accurately measure a concentration of sulfur trioxide in gas sample 105, according to one embodiment, the optical radiation source 120 is tuned over one or more infrared frequencies, and the optical signal 123 transmitted through the gas sample 105 is monitored by the optical detector 125 to determine an amount of optical absorption by the gas sample 105.

By way of a non-limiting example, optical radiation source 120 can be a laser system such as a distributed feedback (DFB) quantum cascade pulsed room temperature laser system, a DFB quantum cascade CW room temperature laser system, an external cavity diode laser system, an optical parametric oscillator laser system, etc.

In order to spectrally resolve the measurements of sulfur trioxide in an environment containing sulfur dioxide and water vapor, various different techniques could be used. For instance, the system and method as discussed herein can utilize different techniques such as scanned and fixed frequency absorption, balanced radiometric detection, frequency modulated (FM) spectroscopy, cavity-ring down, stark modulation, evanescent wave, photothermal deflection, optogalvanic spectroscopy, photoacoustic spectroscopy, etc.

As discussed above, the analyzer 140 can include pressure controller 130 to maintain the gas sample 105 at a sub-atmospheric pressure to yield a good balance between signal strength and isolation of neighboring spectral transitions. For example, in one embodiment, the pressure controller can control the pressure of the gas sample 105 to a sub-atmospheric pressure of substantially near 50 Torr (+/−50 Torr) to optimally measure a concentration of sulfur trioxide.

In accordance with further embodiments, the pressure controller 130 can control the gas sample 105 at a pressure value such as in a pressure range between 10 torr and 200 torr to achieve a balance between receiving a high peak signal and narrow spectroscopic peak absorption transitions.

In addition to controlling a pressure of the gas sample 105, note that embodiments herein can further include controlling a temperature of the gas sample 105 in a temperature value in a temperature range between 200 degrees Celsius and 500 degrees Celsius. Heating of the gas sample 105 can be achieved by activating a heating coil wrapped around a conduit through which the gas sample 105 travels.

Using a sub-atmospheric pressure between 10 torr and 200 torr decreases the pressure broadening of the different spectroscopic transitions, thereby isolating the different absorption features from each other. For example, the pressure controller 130 adjusts a pressure of the gas sample 105 to enhance a differentiation of multiple peak sulfur trioxide absorption frequencies residing in the range of frequencies between approximately 1396 and 1398 (or more specifically, 1396.889 $cm^{-1}$ and 1397.052 $cm^{-1}$). This enables species-specific measurements to be made without interference from primary bath gas constituents in the gas sample 105.

Thus, certain embodiments herein can be characterized as species selective, interference-free, quick, highly-resolved, and an affordable way of detecting a concentration of sulfur trioxide in a gas sample 105. The analyzer 140 as discussed herein can be readily applied for making sulfur trioxide measurements in any suitable measurement site, including power plants and combustion engines.

The particular isolated sulfur trioxide transitions at 1396.889 $cm^{-1}$, 1396.908 $cm^{-1}$, 1396.962 $cm^{-1}$, 1396.944 $cm^{-1}$, 1396.958 $cm^{-1}$, 1396.962 $cm^{-1}$, 1397.003 $cm^{-1}$, 1397.037 $cm^{-1}$, 1397.047 $cm^{-1}$, or 1397.052 $cm^{-1}$ provide substantial absorption of optical energy. However, such absorption bands are isolated from absorption bands associated with both sulfur dioxide and water vapor. Thus, embodiments herein can take advantage of implementing so-called middle infrared lasers that have become commercially available in the last several years. Performing the measurements at controlled pressure achieves better isolation between the target transition and neighboring locations. Though sub-atmospheric pressure is suitable in general, 50 Torr may be a near optimal pressure for measuring sulfur trioxide because that pressure achieves a balance between highest signal and narrowest, i.e. most isolated, transitions.

Figure 2:
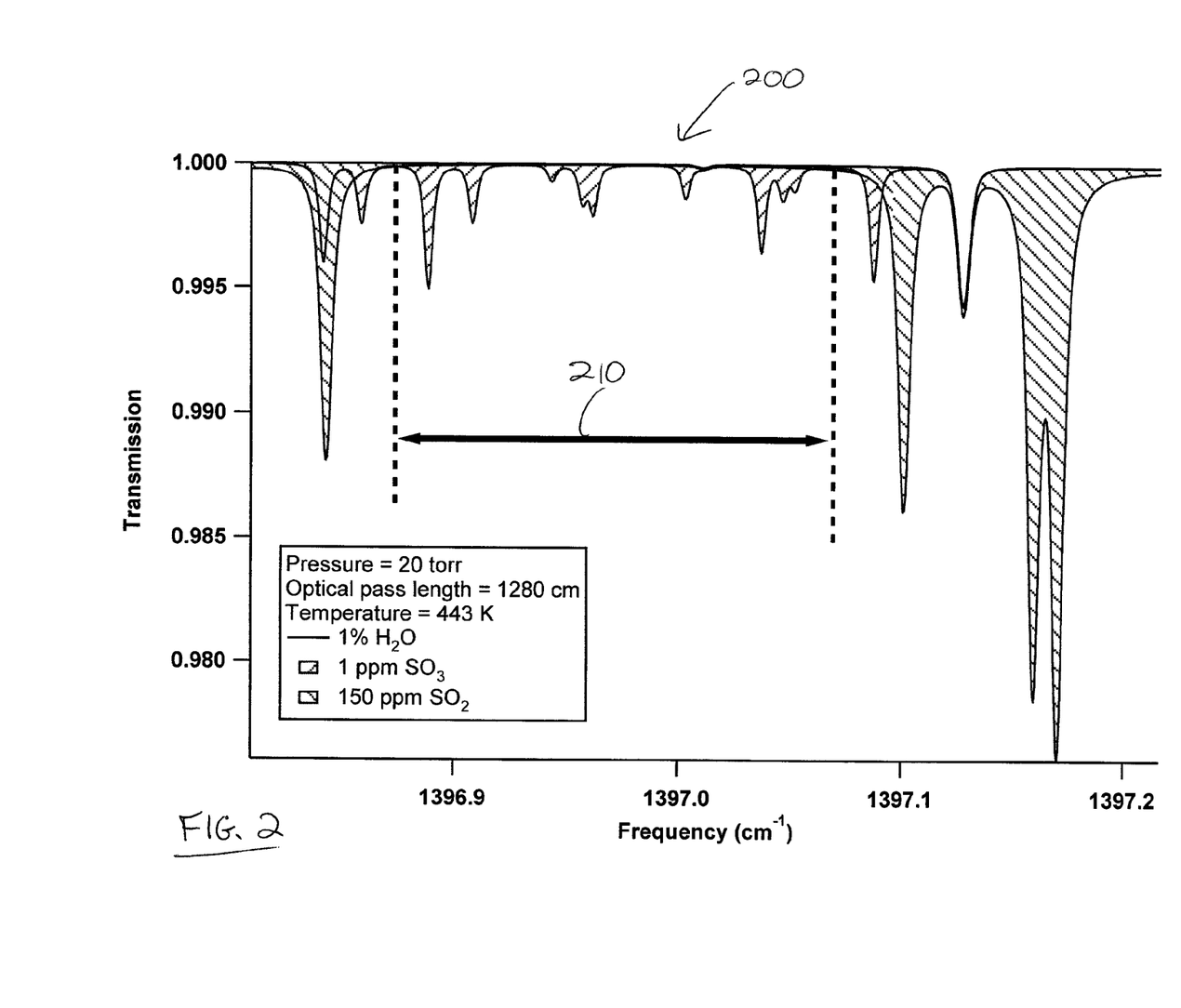
FIG. 2 is an example theoretical graph illustrating transmission/absorption of optical radiation by a gas sample at different frequencies according to embodiments herein.

FIG. 2 is an example graph 200 illustrating hypothetical transmission/absorption of optical radiation by a gas sample 105 at different frequencies according to embodiments herein. As shown, graph 200 illustrates absorption/transmission of optical energy by water, sulfur trioxide, and sulfur dioxide at different frequencies. As shown, in range 210, there are nine peak sulfur trioxide absorption frequencies where there is little or no interference by water and/or sulfur dioxide. The optical frequencies as discussed herein have never been used in the prior art to detect a concentration of sulfur trioxide. These frequencies may not be optimum for detection of $SO_3$ in the absence of $SO_2$ and water, as they are not necessarily strongest absorption lines. In one embodiment, due to the gas in this application, the selected nine peaks may be the best balance between absorption strength and lack of interference caused by $SO_2$ and water present in the gas sample.

Figure 3:
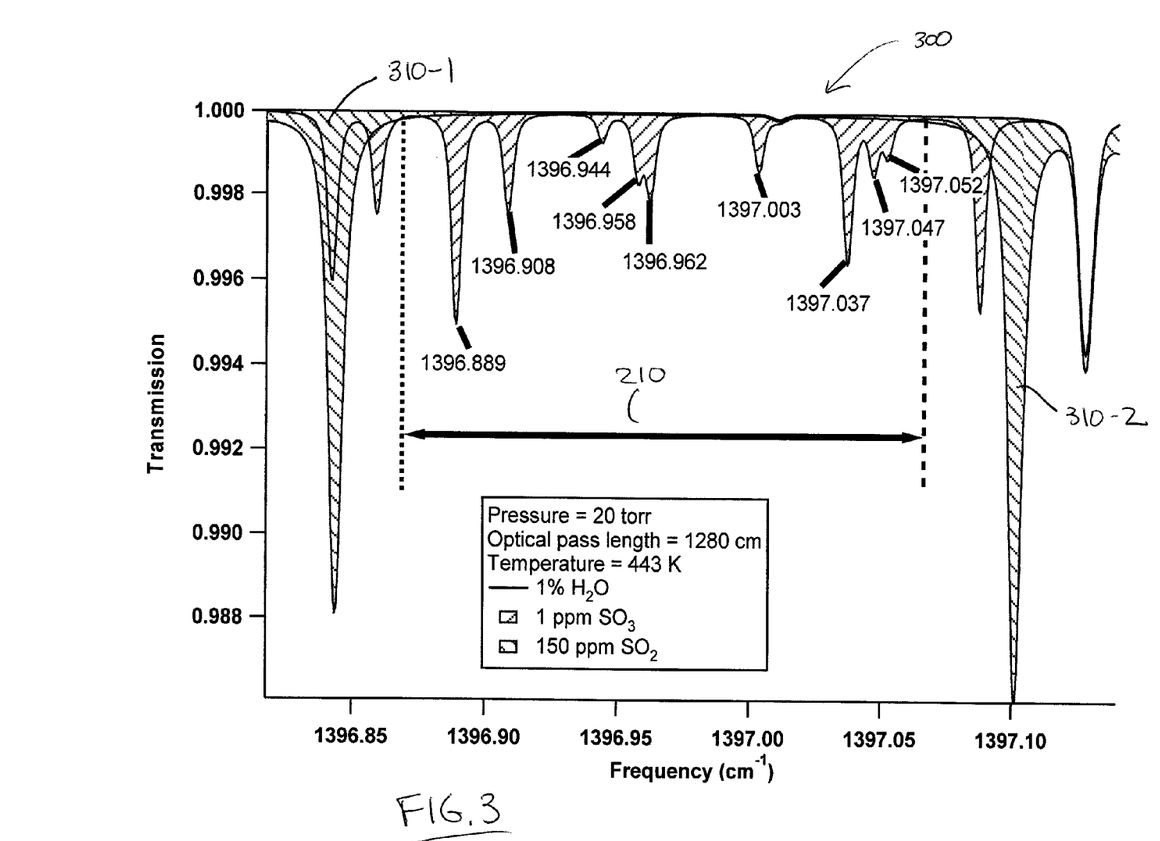
FIG. 3 is an example theoretical graph illustrating transmission/absorption of optical radiation by a gas sample at different frequencies according to embodiments herein.

FIG. 3 is an example diagram illustrating hypothetical transmission/absorption of optical radiation by a gas sample 105 at different frequencies according to embodiments herein. In range 210, there are nine peak sulfur trioxide absorption frequencies where there is little or no interference by water and/or sulfur dioxide. The sulfur trioxide peaks include a band of absorption frequencies around frequency 1396.889 $cm^{-1}$, 1396.908 $cm^{-1}$, 1396.944 $cm^{-1}$, 1396.958 $cm^{-1}$, 1396.962 $cm^{-1}$, 1397.003 $cm^{-1}$, 1397.037 $cm^{-1}$, 1397.047 $cm^{-1}$, and/or 1397.052 $cm^{-1}$. As shown, the nine sulfur trioxide peaks reside in between two peak sulfur dioxide absorption frequencies (namely, sulfur dioxide peak absorption frequency 310-1 and sulfur dioxide peak absorption frequency 310-2). Note that the two peak sulfur dioxide absorption frequencies 310-1 and 310-2 reside outside of the range of frequencies between 1396.889 cm-1 and 1397.052 $cm^{-1}$.

As shown in this test case, the pressure controller 130 controls the pressure of the gas sample 105 to be 20 torr. Temperature controller 110 controls the temperature of the gas to be 443 Kelvin. Assume in this example that the gas sample 105 contains 1% water, 1 ppm (part per million) sulfur trioxide, and 150 ppm sulfur dioxide. Based on these concentrations, the gas sample 105 absorbs the optical signal 123 as shown in graph 300. As previously discussed, during operation, the optical detector 125 detects the amount of absorption by the gas sample 105 at one or more frequencies in range 210. Based on the detected amount of absorption at one or more peak sulfur trioxide absorption frequencies in range 210, the analyzer 140 generates a value indicative of the amount sulfur trioxide in the gas sample 105.

Note that the method of detecting a concentration of sulfur trioxide can vary depending on the application. For example, in one embodiment, the concentration of sulfur trioxide can be generated based on a magnitude of absorption at any of one or more frequencies in the range 210. In another embodiment, the analyzer 140 calculates the concentration of sulfur trioxide based on a magnitude of absorption at one or more of the peak sulfur trioxide frequencies. In yet further embodiments, the analyzer 140 calculates the concentration of sulfur trioxide based on the absorption area under the curve. More specifically, in this last embodiment, the analyzer 140 can be configured to calculate an amount of absorption of the optical signal by the gas sample 105 in a continuous range of frequencies of the optical signal 123 in a range of frequencies residing between 1396.889 $cm^{-1}$ and 1397.052 $cm^{-1}$.

Figure 4:
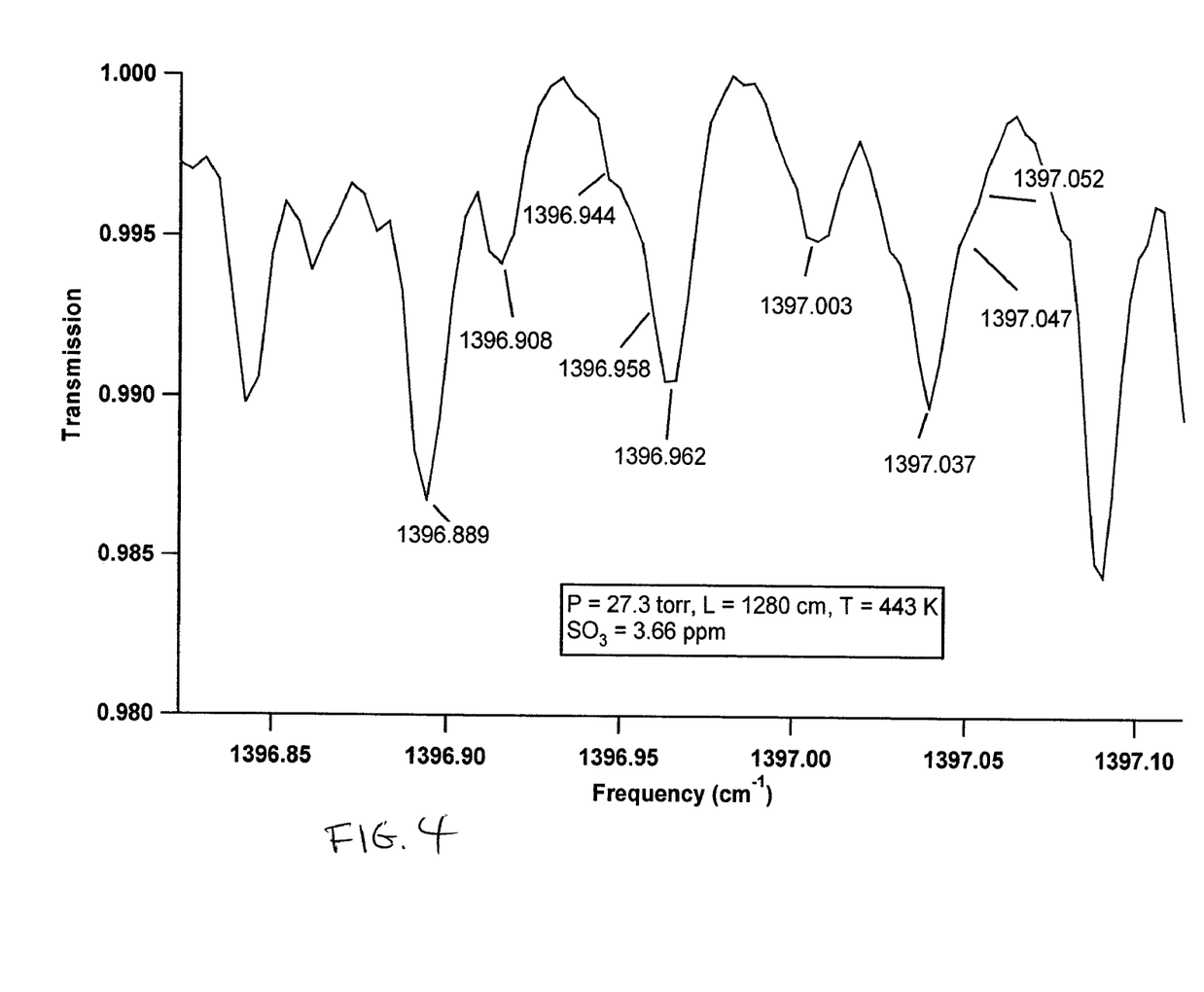
FIG. 4 is an example diagram illustrating an actual sample measurement of transmission/absorption of optical radiation by a gas sample at different frequencies according to embodiments herein.

FIG. 4 is an example diagram illustrating an actual sample measurement of transmission/absorption of optical radiation by a gas sample 105 at different frequencies according to embodiments herein. Graph 400 illustrates optical energy absorption of sulfur trioxide at different frequencies. The analyzer 140 controls the pressure of the gas sample 105 to be 27.3 torr. The analyzer 140 controls the temperature of the gas sample 105 to be approximately 443 Kelvin. Based on absorption of the sulfur trioxide in the range 210, the analyzer 140 calculates the concentration of sulfur trioxide to be 3.66 ppm.

Figure 5:
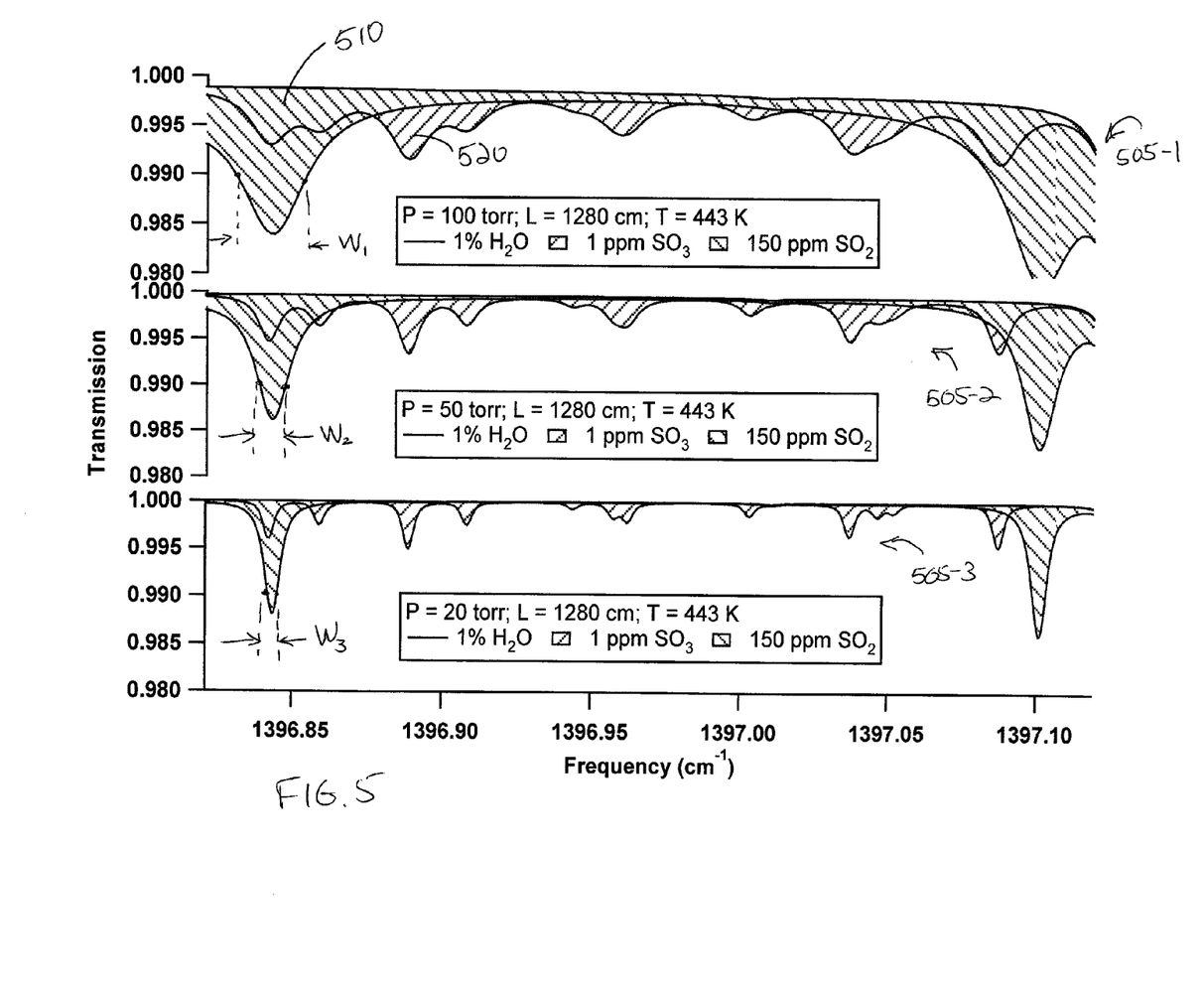
FIG. 5 is an example theoretical graph illustrating how adjusting environmental parameters associated with a gas sample can affect transmission/absorption of optical radiation by a gas sample at different frequencies according to embodiments herein.

FIG. 5 is an example diagram illustrating how adjusting environmental parameters such as pressure and temperature associated with a gas sample 105 can affect transmission/absorption of optical radiation by a gas sample 105 at different frequencies according to embodiments herein.

More specifically, graph 505-1 illustrates a first test case in which the pressure controller 130 controls the pressure of the gas sample 105 to be around 100 torr. Temperature controller 110 controls the temperature of the gas sample 105 to be around 443 Kelvin.

Graph 505-2 illustrates a second test case in which the pressure controller 130 controls the pressure of the gas sample 105 to be around 50 torr. Temperature controller 110 controls the temperature of the gas sample 105 to be around 443 Kelvin.

Graph 505-3 illustrates a third test case in which the pressure controller 130 controls the pressure of the gas sample 105 to be around 20 torr. Temperature controller 110 controls the temperature of the gas sample 105 to be around 443 Kelvin.

In one embodiment, the pressure controller 130 of analyzer 140 adjusts a pressure of the gas sample 105 to reduce interference between a peak sulfur dioxide spectral absorption frequency and a peak sulfur trioxide spectral absorption frequency. For example, the bandwidth of absorption peak 510 associated with sulfur dioxide is so wide that it interferes with absorption peak 520 associated with sulfur trioxide.

As previously discussed, embodiments herein include adjusting the pressure of the gas sample 105 to a value such as 20 torr, 50 torr, etc., to reduce interference such that there is substantially little or no absorption overlap between absorption peak 510 associated with sulfur dioxide and absorption peak 520 associated with sulfur trioxide. In other words, the pressure controller 130 of analyzer 140 can be configured to adjust a pressure of the gas sample 105 reduce interference at the absorption peaks to enhance a differentiation of multiple peak sulfur trioxide absorption frequencies residing in a range of frequencies between 1396.889 cm$^{-1}$ and 1397.052 cm$^{-1}$.

In yet further embodiments, the pressure controller 130 controls a pressure of the gas sample to reduce an absorption bandwidth of the optical signal around a peak spectral absorption frequency associated with the sulfur trioxide. For example, note that the absorption bandwidth W3 is narrower than absorption bandwidth W2; absorption bandwidth W2 is narrower than absorption bandwidth W1. These graphs 500 therefore indicate how to adjust a pressure of the gas sample 105 to narrow the absorption bandwidths. As mentioned above, adjusting the pressure in this manner reduces interference between spectral absorption peaks and enables more accurate calculation of the concentration of sulfur trioxide.

Figure 6:
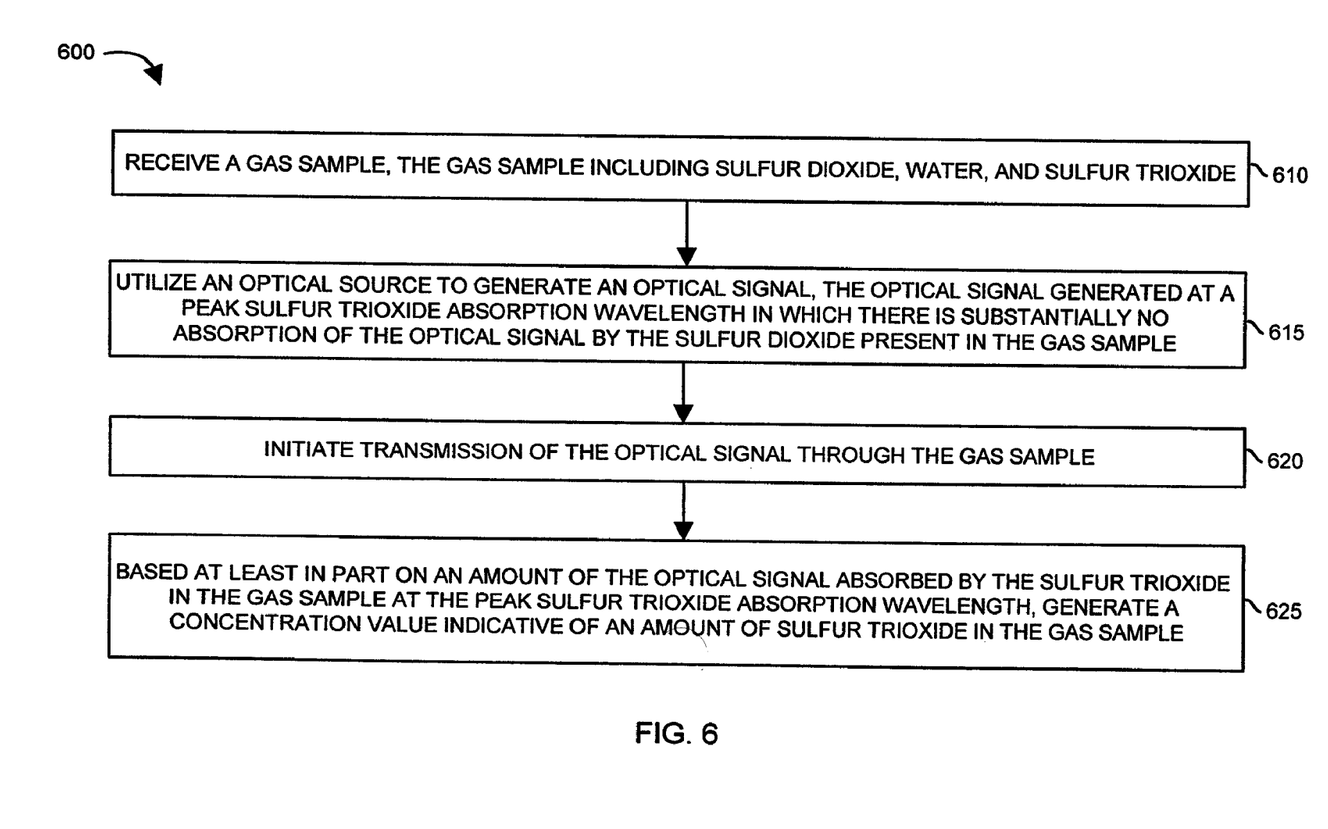
FIG. 6 is an example flowchart illustrating a method of calculating a concentration of sulfur trioxide according to embodiments herein.

FIG. 6 is a flowchart 600 illustrating a method of controlling system parameters and analyzing a gas sample 105 according to embodiments herein. Note that there will be some overlap with respect to concepts as discussed above for FIGS. 1 through 5.

In step 610, the analyzer 140 receives a gas sample 105. The gas sample 105 can include different gases such as sulfur dioxide, water, and/or sulfur trioxide.

In step 615, the analyzer 140 utilizes optical radiation source 120 to generate an optical signal 123. In one embodiment, the optical radiation source 120 generates the optical signal 123 at one or more peak sulfur trioxide absorption frequencies in which there is substantially no absorption of the optical signal by the sulfur dioxide present in the gas sample 105.

In step 620, the analyzer 140 initiates transmission of the optical signal 123 through the gas sample 105.

In step 625, based at least in part on an amount of the optical signal 123 absorbed by the sulfur trioxide in the gas sample at the one or more peak sulfur trioxide absorption frequencies, the analyzer 140 generates a concentration value indicative of an amount of sulfur trioxide in the gas sample 105.

Figure 7:
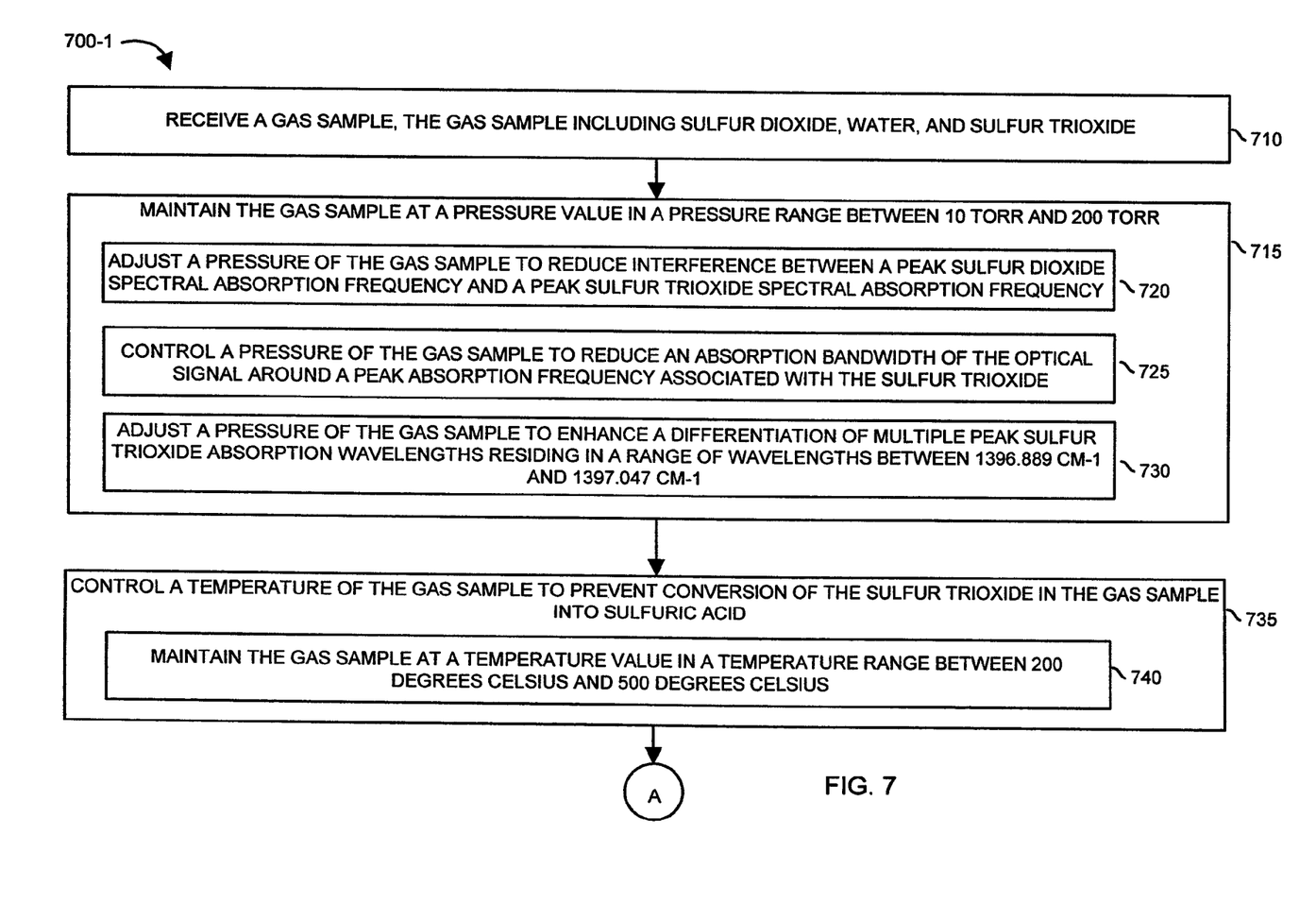
FIGS. 7 and 8 combine to form an example flowchart illustrating a method of calculating a concentration of sulfur trioxide according to embodiments herein.
Figure 8:
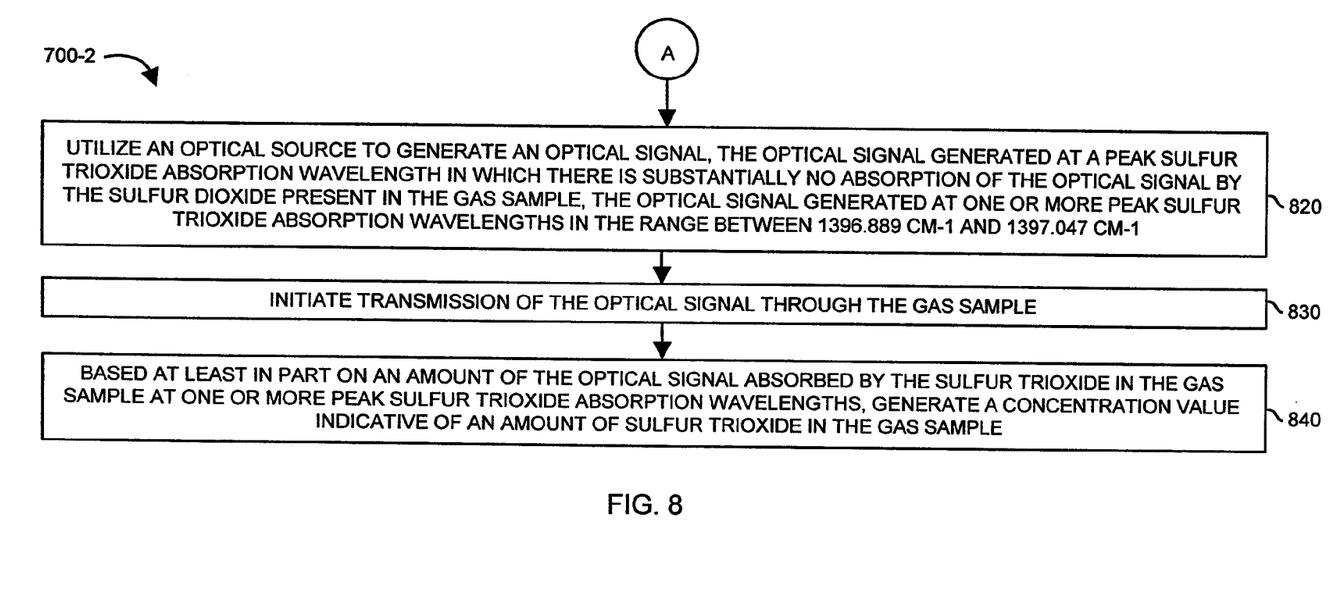

FIGS. 7 and 8 combine to form a flowchart 700 (e.g., flowchart 700-1 and flowchart 700-2) illustrating a method of analyzing a gas sample 105 according to embodiments herein. Again, note that there will be some overlap with respect to concepts discussed above.

Referring now to flowchart 700-1 in FIG. 7, in step 710, the analyzer 140 receives a gas sample 105. As previously discussed, the gas sample 105 can include contaminants such as sulfur dioxide, water, and sulfur trioxide as well as other possible contaminants.

In step 715, the analyzer 140 maintains the gas sample at a pressure value in a pressure range between 10 torr and 200 torr. Note that setting of the pressure between 10 torr and 100 torr is shown by way of non-limiting example only and that the gas sample 105 can be maintained at any suitable pressure for measuring the concentration of sulfur trioxide in the gas sample 105.

In step 720, the analyzer 140 adjusts a pressure of the gas sample 105 to reduce interference between a peak sulfur dioxide spectral absorption frequency and a peak sulfur trioxide spectral absorption frequency.

In step 725, the analyzer 140 controls a pressure of the gas sample 105 to reduce an absorption bandwidth of the optical signal 123 around a peak absorption frequency associated with the sulfur trioxide.

In step 730, the analyzer 140 adjusts a pressure of the gas sample 105 to enhance a differentiation of multiple peak sulfur trioxide absorption frequencies residing in a range of frequencies between 1396.889 cm$^{-1}$ and 1397.052 cm$^{-1}$.

In step 735, the analyzer 140 controls a temperature of the gas sample 105 to prevent conversion of sulfur trioxide in the gas sample 105 into sulfuric acid. In one embodiment, by way of a non-limiting example, to prevent conversion into sulfuric acid, the analyzer 140 controls a temperature of the gas sample 105 to be in a range between 200 degrees Celsius and 500 degrees Celsius.

In step 740, by way of a non-limiting example, the analyzer 140 maintains the gas sample 105 at a temperature value in a temperature range between 200 degrees Celsius and 500 degrees Celsius. A higher temperature helps prevent the $SO_3$ from converting to $H_2SO_4$ in the presence of water.

Referring now to flowchart 700-2 in FIG. 8, in step 820, the analyzer 140 utilizes an optical source 120 to generate an optical signal 123. The optical signal 123 is generated at a peak sulfur trioxide absorption frequency in which there is substantially no absorption of the optical signal by the sulfur dioxide and/or water present in the gas sample 105. The optical signal can be generated at one or more peak sulfur trioxide absorption frequencies in the range between 1396.889 cm$^{-1}$ and 1397.052 cm$^{-1}$.

In step 830, the analyzer 140 initiates transmission of the optical signal 123 through the gas sample 105.

In step 840, based at least in part on an amount of the optical signal 123 absorbed by the sulfur trioxide in the gas sample 105 at one or more peak sulfur trioxide absorption frequencies, area under curve, etc., the analyzer 140 generates a concentration value indicative of an amount of sulfur trioxide in the gas sample 105.

Figure 9:
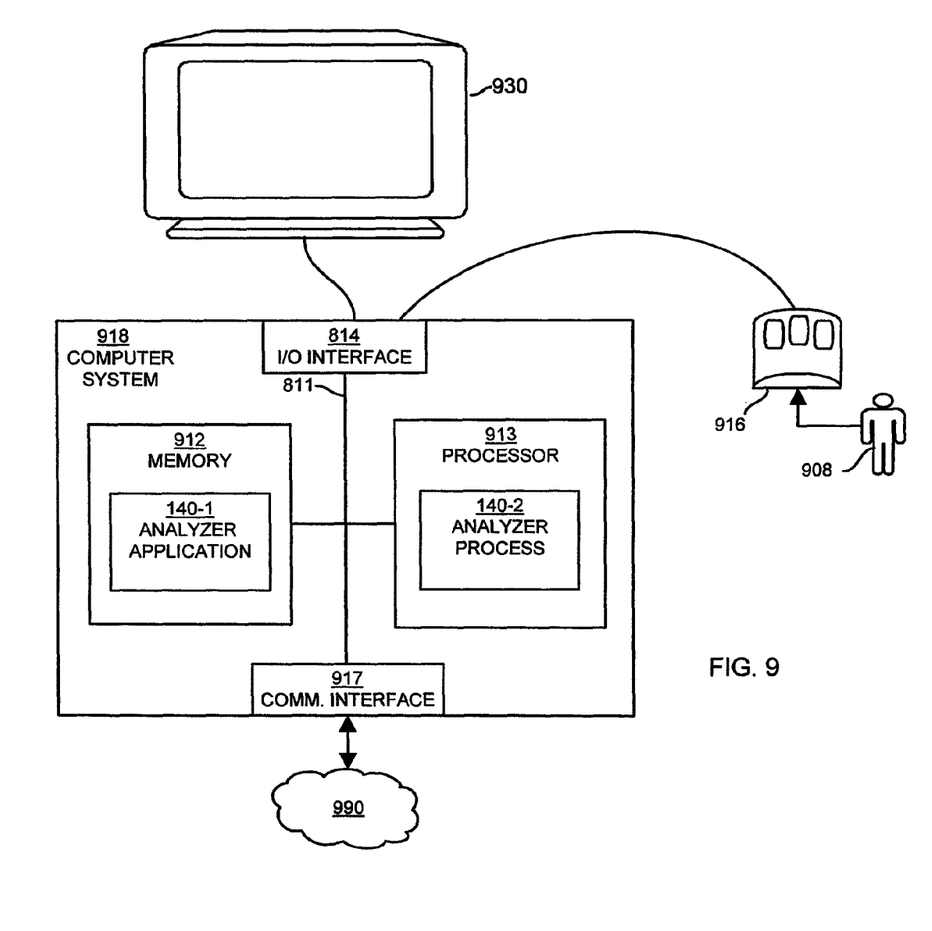
FIG. 9 is an example diagram illustrating of an architecture for implementing an analyzer according to embodiments herein.

FIG. 9 is a block diagram of an example architecture of a respective computer system 918 such as one or more computers, processes, etc., for implementing analyzer 140 and/or control of other system conditions according to embodiments herein. In other words, the analyzer 140 can include hardware and/or software that controls and/or communicates with devices such as temperature controller 110, optical radiation source 120, pressure controller 130, optical detector 125, etc., to facilitate generation of a value indicative of concentration of sulfur trioxide in the gas sample 105.

Computer system 918 can include one or more computerized devices such as personal computers, workstations, portable computing devices, consoles, network terminals, networks, processing devices, etc.

Note that the following discussion provides a basic example embodiment indicating how to carry out all or portions of the functionality associated with the analyzer 140 or other devices as discussed above and below. However, it should be noted again that the actual configuration for carrying out the analyzer 140 can vary depending on a respective application. For example, as previously discussed, computer system 918 can include one or multiple computers that carry out the processing as described herein.

As shown, computer system 918 of the present example includes an interconnect 811 coupling memory system 912, a processor 913, I/O interface 914, and a communications interface 917.

I/O interface 914 provides connectivity to peripheral devices such as repository and other devices 916 (if such devices are present) such as a keyboard, mouse (e.g., selection tool to move a cursor), display screen 930, etc.

In one embodiment, communications interface 917 enables the analyzer application 140-1 of computer system 918 to communicate over network 990 and, if necessary, retrieve and data, update information, etc., to and from different sources.

As shown, memory system 912 can be encoded with instructions associated with analyzer application 140-1. The instructions support functionality as discussed above and as discussed further below. The analyzer application 140-1 (and/or other resources as described herein) can be embodied as software code such as data and/or logic instructions on a tangible and/or intangible computer readable medium, media, etc. such as memory or on another computer readable medium that supports processing functionality according to different embodiments described herein.

During operation of one embodiment, processor 913 accesses memory system 912 via the use of interconnect 811 in order to launch, run, execute, interpret or otherwise perform the logic instructions of the analyzer application 140-1. Execution of the analyzer application 140-1 produces processing functionality in analyzer process 140-2. In other words, the analyzer process 140-2 represents one or more portions of the analyzer 140 performing within or upon the processor 913 in the computer system 918.

It should be noted that, in addition to the analyzer process 140-2 that carries out method operations as discussed herein, other embodiments herein include the analyzer application 140-1 itself such as the un-executed or non-performing logic instructions and/or data, etc. The analyzer application 140-1 may be stored on a computer readable medium such as a floppy disk, hard disk or in an optical medium. According to other embodiments, the analyzer application 140-1 can also be stored in a memory type system such as in firmware, read only memory (ROM), or, as in this example, as executable code within the memory system 912 (e.g., within Random Access Memory or RAM).

Note again that techniques herein are well suited for use in detecting contaminants in a gas sample 105 such as sulfur trioxide. However, it should be noted that embodiments herein are not limited to use in such applications and that the techniques discussed herein are suited for other applications as well.

While this invention has been particularly shown and described with references to preferred embodiments thereof, it will be understood by those skilled in the art that various changes in form and details may be made therein without departing from the spirit and scope of the present application as defined by the appended claims. Such variations are intended to be covered by the scope of this present application. As such, the foregoing description of embodiments of the present application is not intended to be limiting. Rather, any limitations to the invention are presented in the following claims.

We claim:

1. A method comprising:
   receiving a gas sample, the gas sample including sulfur dioxide, water, and sulfur trioxide;
   utilizing an optical source to generate an optical signal, the optical signal generated at a peak sulfur trioxide absorption frequency in which there is substantially no absorption of the optical signal by the sulfur dioxide present in the gas sample, the peak sulfur trioxide absorption frequency being a frequency in a range of frequencies from 1396.889 $cm^{-1}$ to 1397.052 $cm^{-1}$ inclusive;
   initiating transmission of the optical signal through the gas sample;
   measuring an amount of the optical signal absorbed by the sulfur trioxide in the gas sample at the peak sulfur trioxide absorption frequency; and
   based at least in part on the measured amount of the optical signal absorbed by the sulfur trioxide in the gas sample at the peak sulfur trioxide absorption frequency, generating a concentration value indicative of an amount of sulfur trioxide in the gas sample.

2. The method as in claim 1 further comprising:
   maintaining the gas sample at a pressure value in a pressure range between 10 torr and 200 torr.

3. The method as in claim 2 further comprising:
   maintaining the gas sample at a temperature value in a temperature range between 200 degrees Celsius and 500 degrees Celsius.

4. The method as in claim 1 further comprising:
   adjusting a pressure of the gas sample to reduce interference between a peak sulfur dioxide absorption frequency and the peak sulfur trioxide absorption frequency.

5. The method as in claim 2 further comprising:
   controlling a pressure of the gas sample to reduce an absorption bandwidth of the optical signal around the peak sulfur trioxide absorption frequency; and
   controlling a temperature of the gas sample to prevent conversion of the sulfur trioxide in the gas sample into sulfuric acid.

6. The method as in claim 5, wherein controlling a pressure of the gas sample includes:

adjusting a pressure of the gas sample to enhance a differentiation of multiple peak sulfur trioxide absorption frequencies residing in the range of frequencies from 1396.889 cm$^{-1}$ to 1397.052 cm$^{-1}$ inclusive.

7. The method as in claim 6, wherein the multiple peak sulfur trioxide absorption frequencies reside between two peak sulfur dioxide absorption frequencies, the two peak sulfur dioxide absorption frequencies being outside of the range of frequencies from 1396.889 cm$^{-1}$ to 1397.052 cm$^{-1}$ inclusive.

8. The method as in claim 7, wherein the optical signal is generated at the multiple peak sulfur trioxide absorption frequencies in the range from 1396.889 cm$^{-1}$ to 1397.052 cm$^{-1}$, inclusive, and
wherein the concentration value indicative of the amount of sulfur trioxide in the gas sample is generated based at least in part on an amount of the optical signal absorbed by the sulfur trioxide in the gas sample at the multiple peak sulfur trioxide peak absorption frequencies.

9. The method as in claim 8, wherein the multiple peak sulfur trioxide absorption frequencies include at least two sulfur trioxide absorption peaks selected from a group consisting of:
a peak sulfur trioxide absorption frequency around 1396.889 cm$^{-1}$
a peak sulfur trioxide absorption frequency around 1396.908 cm$^{-1}$
a peak sulfur trioxide absorption frequency around 1396.944 cm$^{-1}$
a peak sulfur trioxide absorption frequency around 1396.958 cm$^{-1}$
a peak sulfur trioxide absorption frequency around 1396.962 cm$^{-1}$
a peak sulfur trioxide absorption frequency around 1397.003 cm$^{-1}$
a peak sulfur trioxide absorption frequency around 1397.037 cm$^{-1}$
a peak sulfur trioxide absorption frequency around 1397.047 cm$^{-1}$, and
a peak sulfur trioxide absorption frequency around 1397.052 cm$^{-1}$.

10. The method as in claim 6, wherein generating the concentration value indicative of the amount of sulfur trioxide in the gas sample further comprises:
calculating an amount of absorption of the optical signal by the gas sample in a continuous range of frequencies of the optical signal, the continuous range of frequencies residing from 1396.889 cm$^{-1}$ to 1397.052 cm$^{-1}$ inclusive.

11. A system comprising:
an optical source to generate an optical signal, the optical signal generated at a peak sulfur trioxide absorption frequency in which there is substantially no absorption of the optical signal by sulfur dioxide, the peak sulfur trioxide absorption frequency being a frequency in a range of frequencies from 1396.889 cm$^{-1}$ to 1397.052 cm$^{-1}$ inclusive;
a controller to initiate transmission of the optical signal through a gas sample, the gas sample including sulfur dioxide, water, and sulfur trioxide; and
an analyzer to generate a concentration value indicative of an amount of sulfur trioxide in the gas sample based at least in part on an amount of the optical signal absorbed by the sulfur trioxide in the gas sample at the peak sulfur trioxide absorption frequency.

12. The system as in claim 11 further comprising:
a pressure controller to maintain the gas sample at a pressure value in a pressure range between 10 torr and 200 torr.

13. The system as in claim 12 further comprising:
a temperature controller to maintain the gas sample at a temperature value in a temperature range between 200 degrees Celsius and 500 degrees Celsius.

14. The system as in claim 11 further comprising:
a pressure controller to adjust a pressure of the gas sample to reduce interference between a peak sulfur dioxide absorption frequency and the peak sulfur trioxide absorption frequency.

15. The system as in claim 12 further comprising:
a pressure controller to control a pressure of the gas sample to reduce an absorption bandwidth of the optical signal around the peak sulfur trioxide absorption frequency.

16. The system as in claim 15, wherein the pressure controller adjusts a pressure of the gas sample to enhance a differentiation of multiple peak sulfur trioxide absorption frequencies residing in the range of frequencies from 1396.889 cm$^{-1}$ to 1397.052 cm$^{-1}$ inclusive.

17. The system as in claim 16, wherein the multiple peak sulfur trioxide absorption frequencies reside between two peak sulfur dioxide absorption frequencies, the two peak sulfur dioxide absorption frequencies being outside of the range of frequencies from 1396.889 cm$^{-1}$ to 1397.052 cm$^{-1}$ inclusive.

18. The system as in claim 17, wherein the optical signal is generated at the multiple peak sulfur trioxide absorption frequencies in the range from 1396.889 cm$^{-1}$ to 1397.052 cm$^{-1}$ inclusive; and
wherein the generator generates the concentration value indicative of the amount of sulfur trioxide in the gas sample based at least in part on an amount of the optical signal absorbed by the sulfur trioxide in the gas sample at the multiple peak sulfur trioxide peak absorption frequencies.

19. The system as in claim 18, wherein the optical signal is generated at multiple peak sulfur trioxide absorption frequencies selected from a group consisting of:
a peak sulfur trioxide absorption frequency around 1396.889 cm$^{-1}$
a peak sulfur trioxide absorption frequency around 1396.908 cm$^{-1}$
a peak sulfur trioxide absorption frequency around 1396.944 cm$^{-1}$
a peak sulfur trioxide absorption frequency around 1396.958 cm$^{-1}$
a peak sulfur trioxide absorption frequency around 1396.962 cm$^{-1}$
a peak sulfur trioxide absorption frequency around 1397.003 cm$^{-1}$
a peak sulfur trioxide absorption frequency around 1397.037 cm$^{-1}$,
a peak sulfur trioxide absorption frequency around 1397.047 cm$^{-1}$, and
a peak sulfur trioxide absorption frequency around 1397.052 cm$^{-1}$.

20. The system as in claim 16, wherein the analyzer calculates an amount of absorption of the optical signal by the gas sample in a continuous range of frequencies of the optical signal, the continuous range of frequencies residing from 1396.889 cm$^{-1}$ to 1397.052 cm$^{-1}$ inclusive.

* * * * *